United States Patent [19]

Kim et al.

[11] Patent Number: 4,960,930

[45] Date of Patent: Oct. 2, 1990

[54] PROCESS FOR PURIFICATION AND RECOVERY OF L-PHENYLALANINE

[75] Inventors: Jong S. Kim; Min S. Han; Bun S. Lim; Gae C. Lee; Seung T. Lee, all of Seoul, Rep. of Korea

[73] Assignee: Miwon Co., Ltd., Seoul, Rep. of Korea

[21] Appl. No.: 423,887

[22] Filed: Oct. 19, 1989

[51] Int. Cl.$^5$ ............................................. C07C 227/40
[52] U.S. Cl. ....................................... 562/443; 556/134
[58] Field of Search ................... 562/443, 402; 556/134

[56] References Cited

U.S. PATENT DOCUMENTS

| | | | |
|---|---|---|---|
| 3,758,559 | 9/1973 | Bollinger | 562/443 |
| 3,853,906 | 12/1974 | Rogozhin et al. | 562/402 |
| 3,916,004 | 10/1975 | Okada et al. | 556/134 |
| 4,399,304 | 8/1983 | Matsuishi et al. | 562/445 |
| 4,584,399 | 4/1986 | Portal et al. | 562/443 |
| 4,621,153 | 11/1986 | Hatch | 562/443 |

FOREIGN PATENT DOCUMENTS 1019574  2/1966  United Kingdom ................ 562/443

OTHER PUBLICATIONS

Malic et al., Chem. Abst., vol. 89, #118619z (1978).
Cogan et al., J. Sci. Food & Agri., 32, 459–66 (1981).
Abe et al., Bull., Chem. Soc. Jpn. 55, 687–89 (1982).
C. S. Cleaver, R. A. Hardy, Jr. and H. G. Cassidy, J. Am. Chem. Soc. 67, 1343 (1945).

*Primary Examiner*—James H. Reamer
*Attorney, Agent, or Firm*—Birch, Stewart, Kolasch & Birch

[57] ABSTRACT

A process for purification and recovery of phenylalanine from a microbial fermentation broth containing phenylalanine which comprises providing a zinc salt of phenylalanine at a pH of 7–9, adding acid at a pH of 4–7, and separating precipitated phenylalanine.

8 Claims, No Drawings

PROCESS FOR PURIFICATION AND RECOVERY OF L-PHENYLALANINE

BACKGROUND OF THE INVENTION

1. Field of the Invention

The present invention relates to a process for purification and recovery of L-phenylalanine (hereinafter "phenylalanine") and more particularly, to a process for purification and recovery of phenylalanine from mixtures containing phenylalanine and undesired impurities, typically from microbial fermentation broths used in the microbial production of phenylalanine.

2. Description of the Prior Art

Generally, amino acids produced by a microorganism have to be recovered from fermentation broths containing inorganic salts, other amino acids, peptides, other organic compounds, cell debris, enzymes, and other proteins. Phenylalanine traditionally has been difficult to purify and recover from fermentation broths since phenylalanine is recovered from fermentation broths containing a large amount of impurities such as nutrients, peptides, organic or inorganic compounds, cell debris, enzymes, etc.

Several methods of amino acid recovery and purification have been described in the prior art.

(1) One specific method involves an ion exchange resin. The ion exchange method utilizes an anion or a cation exchange resin in a column which adsorbs the amino acid under an appropriate pH to separate it from the reaction mixture by using acid or alkalis. Such conventional methods are shown in U.S. Pat. No. 4,584,399 to Portal et al; Cogan et al., J. Sci. Food & Agri., 32, 459-66 (1981); Abe et al., Bull, Chem Soc. Jpn. 55, 687-89, (1982)0. Lutz, Br. Jirgensons, Ber., 64, 1221 (1931); D.T. Englis and H.A. Fiess, Ind. Eng. Chem., 36, 604 (1944); and C.S. Cleaver, R.A. Hardy, Jr. and H.G. Cassidy, J.Am. Chem. Soc., 67, 1343 (1945).

(2) U.S. Pat. No. 4,399,304 to Matsuishi et al. discloses a process for recovery of phenylalanine which comprises reacting phenylalanine in a fermentation broth with sulfuric acid to produce phenylalanine ½ sulfate ½ hydrate and recovering it from the fermentation broth.

(3) U.S. Pat. No. 4,621,153 to Hatch discloses a method of recovering an amino acid from a mixture by providing a source of bivalent metal ions (calcium) capable of forming a complex with the amino acid at pH 8.5-11.

However, such ion exchange methods (1) require a large amount of acids or alkalis as an eluting agent and expensive equipment for ion exchange resin towers. Such sulfate methods (2) require a strong sulfuric acid. Furthermore, it is difficult to obtain ½ sulfate ½ hydrate salt of phenylalanine. Also, such calcium salt methods (3) are provided with a final product which has impurities so that they have lower yield.

SUMMARY OF THE INVENTION

Accordingly, it is an object of the present invention to provide an improved process for purification and recovery of phenylalanine in a high yield.

Another object of the present invention is to provide a process for purification and recovery of phenylalanine from a fermentation broth used in the microbial production of phenylalanine, which comprises the steps of (a) adding zinc salt to the fermentation broth and adding an alkali compound to the fermentation broth to adjust the pH of the mixture to 7-9 to produce zinc salt of phenylalanine in a crystalline form, (b) recovering the zinc salt of phenylalanine in the crystalline form, (c) adding acid to the zinc salt of phenylalanine in the crystalline form with water to adjust the pH to 4-7 to dissociate the zinc salt of phenylalanine to produce a solution containing phenylalanine and zinc ion, and (d) separating the phenylalanine from the solution of the step (c).

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

DESCRIPTION OF PREFERRED EMBODIMENTS

Referring now in detail to the present invention, there is provided a process for purification and recovery of phenylalanine from a microbial fermentation broth containing phenylalanine.

The present invention is directed to a process for purification and recovery of phenylalanine from a microbial fermentation broth containing phenylalanine, which comprises the steps of (a) adding zinc salt to the fermentation broth at a pH of 7-9 to produce a zinc salt of phenylalanine, (b) recovering zinc phenylalaninate crystals from the fermentation broth, (c) adding acid the zinc phenylalaninate crystals in water at a pH of 4-7 so as to dissociate the zinc phenylalaninate to produce a dissociation solution containing phenylalanine and zinc ion, and (d) separating phenylalanine from the dissociation solution by precipitation.

The zinc phenylalaninate is obtained, after separating microorganisms from the microbial fermentation broth containing phenylalanine, by adding zinc salt with an equivalent molar amount of phenylalanine to the fermentation broth having the microorganisms removed therefrom adjusting the pH of the resulting solution to between 7 and 9 by adding alkali compounds such as ammonium hydroxide so as to react phenylalanine with zinc ion from the zinc salt to precipitate zinc phenylalaninate, and recovering the precipitated zinc phenylalaninate in the form of large plate crystals, in 95% yield. At this time, the zinc phenylalaninate step does not require the use of an ultra filter and R.O. system for the separation of polymers and other impurities from a fermentation broth when compared with the prior art metal phenylalaninates since the zinc phenylalaninate of the present invention is easily precipitated in the reaction mixture solution. The alkali compounds according to the present invention include sodium hydroxide, potassium hydroxide, ammonium hydroxide, and the like. The zinc salts according to the present invention are zinc chloride, zinc sulfate, zinc acetate $Zn(CH_3COO)_2$.

In the process of the present invention, the phenylalanine is dissociated from the zinc phenylalaninate crystals by suspending the zinc phenylalaninate crystals in water, and adding acid such as a 35% hydrochloric acid to the suspension solution to convert the alkali solution to an acid solution so as to dissociate the zinc phenylalaninate into phenylalanine and zinc ion (zinc chloride). The acids of the present invention include hydrochloric acid, sulfuric acid, phosphoric acid, and the like.

The phenylalanine crystals are obtained by concentrating the dissociation solution, and precipitating only phenylalanine due to the lower solubility of the phenylalanine as compared to zinc chloride.

The phenylalanine crystal is separated by filtering and the filtrate can be recycled to the initial fermentation broth solution after adjusting the pH thereof.

Each of the zinc salts, that is, zinc chloride ($ZnCl_2$), zinc sulfate ($ZnSO_4$), zinc acetate $Zn(CH_3COO)_2$ in an equivalent molar ratio with respect to the phenylalanine is added to 100 ml of a mixture solution (2% w/v) of the microbial fermentation broth containing phenylalanine (PA) at a pH of 9 with ammonia water so as to produce the zinc salt of phenylalanine as shown in Table 1.

TABLE I

| Zinc Salt | | $ZnCl_2$ | $ZnSO_4$ | ZnOAC |
|---|---|---|---|---|
| filtrate | Zn (%) | 0.01 | 0.14 | 0.09 |
| | PA (%) | 0.05 | 0.41 | 0.29 |
| crystal | Zn (%) | 28.5 | 25.2 | 25.4 |
| | ZPA (wt) | 2.75 | 2.31 | 2.68 | wherein Zn is zinc ion, PA is phenylalanine, % is percentage by weight/volume, and ZPA wt is weight of zinc phenylalaninate in grams.

The zinc chloride at the pH indicated below is added to 100 ml of the mixture solution (2% w/v) of the microbial fermentation broth containing phenylalanine so as to produce the zinc salt of phenylalanine as shown in Table II.

TABLE II

| pH | | 6.5 | 7.5 | 8.5 | 9.5 |
|---|---|---|---|---|---|
| filtrate | Zn (%) | 0.18 | 0.09 | 0.02 | 0.07 |
| | PA (%) | 0.38 | 0.20 | 0.08 | 0.14 |
| crystal | Zn (%) | 19.4 | 25.3 | 27.9 | 26.3 |
| | ZPA (wt) | 2.2 | 2.40 | 2.71 | 2.59 | wherein Zn, PA, %, and ZPA wt are same as above

Each acid of the acids dissociated the phenylalanine from 100 ml of the zinc phenylalaninate suspension solution (2% w/v) produces phenylalanine in a crystalline form as shown in Table III.

TABLE III

| Acid | | 35% HCl | 98% $H_2SO_4$ | 85% $H_3Po_4$ |
|---|---|---|---|---|
| filtrate | — | — | — | — |
| crystal | PA(gr) | 0.2 | 0.12 | 0.08 |
| | purity (%) | 98.9 | 98.4 | 99.5 |
| | PA (wt) | 1.23 | 1.17 | 1.27 | wherein PA and % are same as above, and PA wt is weight of phenylalanine.

In the above Tables I, II, and III, the phenylalanine, that is the L-phenylalanine, is analyzed by using waters HPLC. In the analysis the flow rate is 1.0 ml/min at 5 $\mu$ of reverse phased column (Econosphere $C_{18}$), the eluent is 0.13 M $KH_2PO_4$ of pH 2.5 containing 25 ml of Pic A and 50 ml of acetonitrile per liter and 254 nm is used. The dilution is performed by using deionized water for HPLC. Also, Zn is analyzed by using Perkin Elmer $\Sigma$-2 atomic absorption spectrophotometer. The wave length and the lamp applied are 213.9 nm and zinc hollow cathode, respectively.

The present invention will now be described in more detail in connection with the following examples which should be considered as being exemplary and not limiting the present invention.

EXAMPLE 1

22.4 g of zinc chloride (0.17 M) is added to 1 l of fermented broth of phenylalanine (27 g/l 0.16 M) from which the microorganisms have been removed. The mixture is stirred so as to completely dissolve the zinc chloride. Thereafter, ammonia water is added to the dissolved solution to adjust the pH to 8.5. At that time, zinc phenylalaninate crystals are gradually precipitated (crystal weight: 35.4 g, purity: 99.4%).

After the resulting zinc phenylalaninate crystals slurry is filtered and dried, 20 g of the dried zinc phenylalaninate crystals are suspended in 400 ml of water. 35% of hydrochloric acid is gradually added to the suspension solution to adjust the pH to 4 so as to completely dissolve the crystals. The resulting solution is concentrated to produce phenylalanine crystals. The crystals are washed with water and dried so that 23.3 g of phenylalanine is obtained.

EXAMPLE 2

26.5 g of zinc sulfate (0.17 M) is added to 1 l of fermented broth of phenylalanine (27 g/l, 0.16 M) from which the microorganisms have been removed. The mixture is stirred slowly to completely dissolve the zinc sulfate. Ammonia water is gradually added to the dissolved solution to maintain the pH of 7.5 and then zinc phenylalaninate crystals are obtained (crystal wt: 32.4 g, purity: 99.2%).

After the resulting zinc phenylalaninate crystals slurry is filtered and dried, 10g of the dried zinc phenylalaninate crystals are suspended in 400 ml of water. 35% of hydrochloric acid is slowly added to the suspension solution to adjust the pH to 4 so as to completely dissolve the crystals. The resulting solution is concentrated to produce phenylalanine crystals. The crystals are washed with water and dried so that 21.6 g of phenylalanine is obtained.

EXAMPLE 3

28.5 g of zinc acetate (0.16 M) is added to 1 l of fermented broth of phenylalanine (25 g/l, 0.15 M), from which microorganisms have been removed, and stirred slowly to completely dissolve the zinc acetate. Ammonia water is gradually added to the dissolved solution so as to adjust the pH to 8 and then zinc phenylalaninate crystals are obtained (crystal wt: 31.4 g, purity: 98.4%).

After the resulting zinc phenylalaninate crystals slurry is filtered and dried, 10 g of the dried zinc phenylalaninate crystals are suspended in 200 ml of water. 35% of hydrochloric acid is slowly added to the suspension solution to adjust the pH to 4 so as to completely dissolve the crystals. The resulting solution is concentrated to produce phenylalanine crystals. The crystals are washed with water and dried so that 20.5 g of phenylalanine is obtained.

EXAMPLE 4

19 g of zinc chloride (0.15 M) is added to 1 l of fermented broth from which microorganisms have been removed and the mixture is stirred so as to completely dissolve the zinc chloride. Thereafter, ammonia water is gradually added to the dissolved solution to adjust the pH to 9. At that time, zinc phenylalaninate crystals are gradually precipitated (crystal wt: 30.5 g, purity: 99.4%).

After the resulting zinc phenylalaninate crystals slurry is filtered and dried, 20 g of the dried zinc phenylalaninate crystals are suspended in 1l of water. 85% of phosphoric acid is slowly added to the suspension solution to adjust the pH to 5 so as to completely dissolve the crystals. The resulting solution is concentrated to produce phenylalanine crystals. The crystals are washed with water and dried so that 20.4 g of phenylalanine is obtained.

The invention being thus described, it will be obvious that the sam may be varied in many ways. Such variations are not to be regarded as a departure from the spirit and scope of the invention, and all such modifications as would be obvious to one skilled in the art are intended to be included in the scope of the following claims.

WHAT IS CLAIMED IS

1. A process for purification and recovery of phenylalanine from fermented broth of phenylalanine, which comprises the steps of:
    (a) adding zinc salt to said fermentation broth and adding an alkali compound to said fermentation broth to adjust the pH of said mixture to 7-9 to produce zinc salt of phenylalanine in a crystalline form;
    (b) recovering said zinc salt to phenylalanine in the crystalline form;
    (c) adding acid to said zinc salt to phenylalanine in the crystalline form with water to adjust the pH to 4-7 to dissociate said zinc salt of phenylalanine to produce a solution containing phenylalanine and zinc ion; and
    (d) separating the phenylalanine from said solution of said step (c).

2. The process for purification and recovery of phenylalanine of claim 1, wherein the zinc salt is added in an equivalent molar amount with respect to phenylalanine.

3. The process for purification and recovery of phenylalanine of claim 1, wherein the zinc salt in step (a) is selected from the group consisting of zinc chloride, zinc sulfate, and zinc acetate.

4. The process for purification and recovery of phenylalanine of claim 1, wherein the zinc salt is zinc chloride.

5. The process for purification and recovery of phenylalanine of claim 1, wherein the alkali compound in step (a) is selected from the group consisting of sodium hydroxide, potassium hydroxide, and ammonium hydroxide.

6. The process for purification and recovery of phenylalanine of claim 1, wherein the alkali compound is ammonium hydroxide.

7. The process for purification and recovery of phenylalanine of claim 1, wherein the acid in step (c) is selected from the group consisting of hydrochloric acid, sulfuric acid, and phosphoric acid.

8. The process for purification and recovery of phenylalanine of claim 1, wherein the acid is hydrochloric acid.

* * * * *